United States Patent [19]
Moen

[11] Patent Number: 5,569,210
[45] Date of Patent: Oct. 29, 1996

[54] MULTIPLE DRAW SYRINGE

[76] Inventor: Michael Moen, 401 Mensinger Ave., Modesto, Calif. 95350

[21] Appl. No.: 554,553

[22] Filed: Nov. 6, 1995

[51] Int. Cl.$^6$ .................................................. A61M 3/00
[52] U.S. Cl. ...................... 604/191; 178/760; 178/762
[58] Field of Search .................................. 128/760, 762, 128/763; 604/160, 191, 194, 198, 242, 124

[56] References Cited

U.S. PATENT DOCUMENTS

| Re. 33,952 | 6/1992 | Bonaldo | 128/763 |
|---|---|---|---|
| 3,552,394 | 1/1971 | Horn | 604/191 X |
| 3,604,410 | 9/1971 | Whitacre | 128/762 |
| 3,616,789 | 11/1971 | Grabhorn | 128/762 |
| 4,367,737 | 1/1983 | Kozam et al. | 604/191 |
| 4,381,778 | 5/1983 | Kozam et al. | 604/191 |
| 4,676,256 | 6/1987 | Golden | 128/762 |
| 4,758,231 | 7/1988 | Haber et al. | 604/198 |
| 4,843,017 | 6/1989 | Oberhardt et al. | 436/177 |
| 4,980,297 | 12/1990 | Haynes et al. | 128/760 X |
| 5,070,885 | 12/1991 | Bonaldo | 128/760 X |
| 5,097,842 | 3/1992 | Bonn | 128/762 |
| 5,120,311 | 6/1992 | Sagstetter et al. | 604/110 |
| 5,314,412 | 5/1994 | Rex | 604/191 |
| 5,423,752 | 6/1995 | Haber et al. | 604/191 X |
| 5,478,323 | 12/1995 | Westwood et al. | 604/191 |

FOREIGN PATENT DOCUMENTS

WO92/20281  11/1992  WIPO .................................. 128/763

Primary Examiner—Sam Rimell
Attorney, Agent, or Firm—Gene R. Woodle

[57] ABSTRACT

Embodiments of a multiple draw syringe are disclosed which may be used to draw multiple samples of fluid from a human or animal or other source. The multiple draw syringe includes a protective barrel, a plunger tray, and a needle manifold. Evacuated sample tubes may be placed in the plunger tray and the plunger tray inserted into the rear of the protective barrel. The needle manifold includes a forward projecting drawing needle and a plurality of rearward projecting specimen needles. The needle manifold may be inserted into the front of the protective barrel. The drawing needle may be inserted into a vessel from which a sample is to be taken. The plunger tray may then be pressed forward causing the specimen needles to penetrate the stoppers on the evacuated tubes and placing the vessel in operational contact with the interior of the tubes. The fluid flows through the needle manifold into the tubes. The plunger tray may then be pulled rearward and removed which causes the needle manifold to be pulled rearward and the needle manifold is locked within and completely enclosed by the protective barrel. The needle manifold and the protective barrel may then be safely discarded.

12 Claims, 5 Drawing Sheets

MULTIPLE DRAW SYRINGE

BACKGROUND OF THE INVENTION

1. Field of the Invention

The present invention relates generally to the drawing of fluid samples and more particularly to the drawing of multiple fluid samples through a hollow needle inserted into a human, other animal, or other fluid source.

2. Background Information

The invention presented in the present application is believed to solve, in a simple and effective fashion, a problem which has long plagued medical professionals: simultaneously drawing more than one sample of a fluid, particularly blood, in a manner which greatly reduces the chances of an accidental needle stick. For example, in many states a doctor or other medical professional is required to take two samples of blood from the every newborn baby. The samples may be taken by venipuncture of the newborn or, more commonly, from the umbilical cord. Cord samples may be taken by cord venipuncture or by letting cord blood escape or drip from the cord and collecting a sample of the blood. The later method involves risk of contamination from the various body fluids present during birth. Because diseases such as HIV and certain types of hepatitis may be transmitted by exchange of blood caused by accidental needle sticks, a method of taking such samples in a manner which reduces the chances of accidental needle stick is greatly desired.

Several attempts have been made to at least partially solve problems relating to drawing multiple samples of blood or other fluids with a single needle insertion.

One such attempt is disclosed in the patent to Bonn (U.S. Pat. No. 5,097,842, Mar. 24, 1992) which discloses a device for extracting blood, particularly blood from the umbilical cord, and obtaining two or more samples with a single needle insertion. The device includes a valve housing with a primary nipple in the front and two secondary nipples in the back. The nipples are all connected internally. A valve interposed between the primary and secondary nipples may be set to close the connection between the primary nipple and both secondary nipples or to open the connection between the primary nipple and either of the secondary nipples. Needles may be affixed to the primary nipple and to each of the secondary nipples. Evacuated tubes with stoppers may be forced onto the needles on the secondary nipples. The primary needle may be injected into a blood vessel such as in the umbilical cord and, by manipulation of the valve, blood samples taken into either or both of the evacuated tubes.

Another attempt to solve problems relating to drawing multiple fluid samples is disclosed in Golden (U.S. Pat. No. 4,676,256, Jun. 30, 1987) which discloses a hypodermic device which may be used to draw several samples of blood using one insertion needle and one insertion. The device includes an insertion needle which is attached to a manifold having a number of sockets containing an equal number of upright needles. The tops of the sockets are covered by plugs which may slide within the sockets. Capped vacuum tubes corresponding to the number of samples desired are pushed down into the sockets which causes the plugs to be pushed downward within the socket and the plugs and the caps of the vacuum tubes are pierced by the upright needles. A number of samples corresponding to the number of tubes used may then be collected at one time with one insertion.

The ideal multiple draw syringe provides a method of drawing multiple samples of a body fluid through an insertion needle with only one insertion in a manner which greatly reduces the chances of an accidental needle stick and provides for minimum manipulation of needles. The ideal multiple draw syringe should also be simple, lightweight, compact, easy to use, and inexpensive.

SUMMARY OF THE INVENTION

The present invention provides a multiple draw syringe which includes a plunger tray, a protective barrel, and a needle manifold. Conventional evacuated sample tubes may be placed into depressions in the plunger tray. The front of the plunger tray may then be inserted into the open rearward end of the protective barrel. The needle manifold includes a drawing needle which protrudes forward from the needle manifold and a plurality of specimen needles which protrude rearward from the needle manifold. The specimen needles are in operational contact with the drawing needle through a connecting tube and all needles have relatively sharp points and are hollow. There is a protective cover which covers the drawing needle and screws onto the needle manifold. The needle manifold may be slid into the forward end of the protective barrel with the drawing needle protruding from the protective barrel and the specimen needles inside the protective barrel. The plunger tray may then be pushed forward such that the tops of the stoppers on the evacuated tubes make contact with the rearward ends of the specimen needles. The drawing needle cover may then be removed and the drawing needle inserted into the vessel or other fluid carrier from which the sample is to be taken. The plunger tray may then be pressed forward until the rearward ends of the specimen needles pierce the stoppers on the evacuated tubes, placing the sample fluid in operational contact with the interior of the evacuated tubes. The vacuum in the tubes and any pressure within the vessel or other fluid carrier causes the fluid to flow through the drawing needle, through the connecting tube, through the specimen needles, and into the evacuated tubes. The drawing needle may then be pulled from the vessel or other fluid carrier and the plunger tray may be pulled from the protective barrel. This action causes the needle manifold to be pulled entirely within the protective barrel such that neither the drawing nor the specimen needles are exposed. The protective barrel and the enclosed needles may then be safely discarded and the evacuated tubes removed from the plunger tray.

In a second embodiment, which is operated in the manner described above, the needle manifold may be discarded and the plunger tray and protective barrel reused.

One of the major objects of the present invention is to provide a multiple draw syringe for drawing multiple samples of a fluid through an insertion needle using only one insertion.

Another objective of the present invention is to provide a multiple draw syringe which allows the taking of multiple samples and greatly reduces the chances of an accidental needle stick.

Another objective of the present invention is to provide a multiple draw syringe which provides for minimum manipulation and handling of needles.

Another objective of the present invention is to provide a multiple draw syringe which provides for the drawing or multiple samples with little chance of sample contamination.

Another objective of the present invention is to provide a multiple draw syringe which provides for one hand operation during the sample taking phase of syringe use.

Another objective of the present invention is to provide a multiple draw syringe which may easily and safely discarded after use.

Another objective of the present invention is to provide a multiple draw syringe which is simple, lightweight, compact, easy to use, and inexpensive.

These and other features of the invention will become apparent when taken in consideration with the following detailed description and the drawings.

BRIEF DESCRIPTION OF THE DRAWINGS

FIG. 3A further shows one element in two different positions;

DESCRIPTION OF A PREFERRED EMBODIMENT

Figure 13:
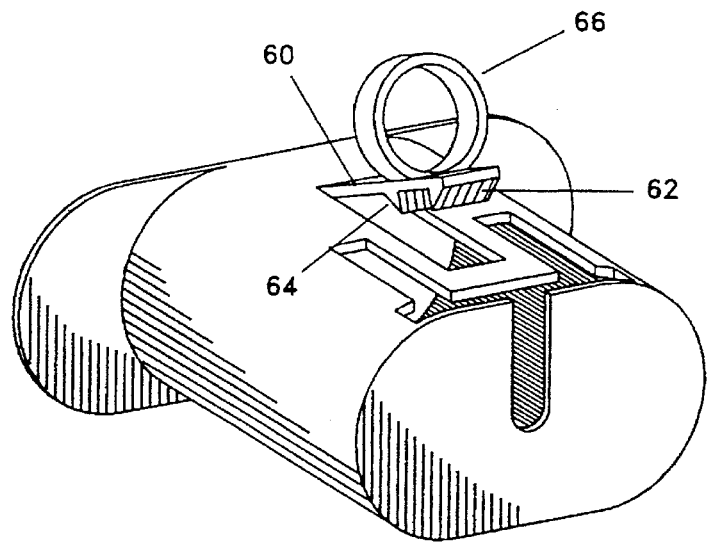
FIG. 13 is a perspective view of a particular element of a second embodiment of a multiple draw syringe of the present invention.

Referring to the drawings, FIGS. 1 through 10, there is shown a preferred form of the multiple draw syringe embodying the present invention. FIGS. 11, 12, and 13 depict a second embodiment of the multiple draw syringe.

Figure 1:
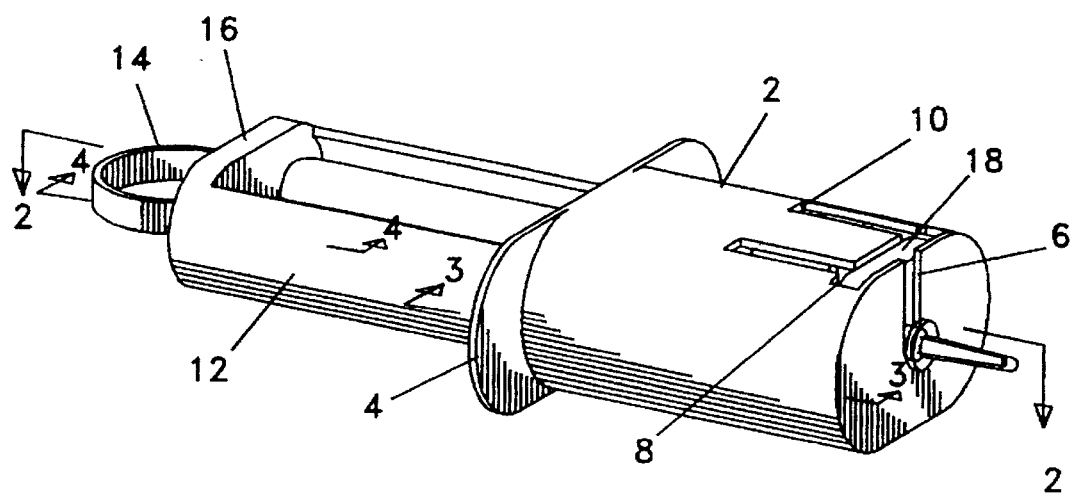
FIG. 1 is a perspective view of a preferred form of a multiple draw syringe of the present invention.

Referring to FIG. 1, there is an a protective barrel 2. The protective barrel 2 is hollow and has an open rearward end and a forward end which is largely closed. Said protective barrel 2 further has an enclosed front side, an enclosed back side, an enclosed bottom, and a top which is largely enclosed. Two finger control wings 4 attached to the rearward end of said protective barrel 2 project outward from the from and back sides of said protective barrel 2. A drawing needle slot 6 forms an opening in the forward end of said protective barrel 2 and starts at slightly below the center of the forward end of said protective barrel 2 and ends at the center of the top of the forward end of said protective barrel 2. A needle manifold slot 8 forms an opening in the top of said protective barrel 2 and is parallel to the forward end of said protective barrel 2. There is a plurality of specimen needle slots 10 which are openings in the top of said protective barrel 2 and which are perpendicular to the manifold slot 8 and which start at the rearward end of said manifold slot 8 and end further rearward on the top of said protective barrel 2.

Still referring to FIG. 1, a plunger tray 12 having the same general shape as said protective barrel 2, but slightly smaller than the interior of said protective barrel 2 may be inserted into the open rearward end of said protective barrel 2. A plunger control ring 14 is attached to the center of the rearward end of the plunger tray 12. The plunger control ring 14 has the general shape of a short cylinder and the top of the cylinder is parallel with the top of said plunger tray 12. Said plunger tray 12 has an open top, front and back walls, and a rearward wall 16.

Still referring to FIG. 1, a needle manifold 18 may be inserted through said manifold slot 8 into the forward end of said protective barrel 2.

Figure 6:
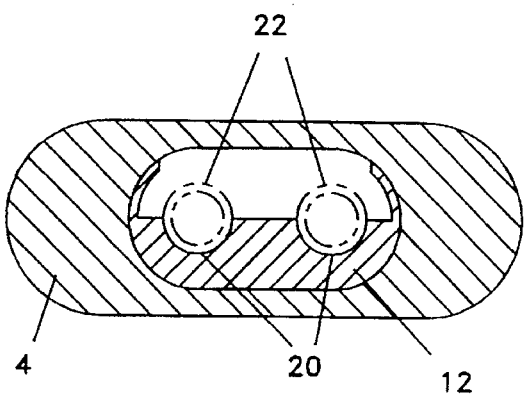
FIG. 6 is a sectional view of the multiple draw syringe taken along line 6—6 of FIG. 2.

Referring now to FIG. 6, the bottom wall of said plunger tray 12 is approximately as thick as half the distance from the top to the bottom of said plunger tray 12. There is a plurality of tube depressions 20 in the top of the bottom of said plunger tray 12. The tube depressions 20 have the general shape of a half cylinder and there is the same number of said tube depressions 20 as the number of said specimen needle slots 10. Said tube depressions 20 are parallel to and aligned vertically with said specimen needle slots 10. Conventional evacuated tubes 22 may be placed in said tube depressions 20.

Figure 4:
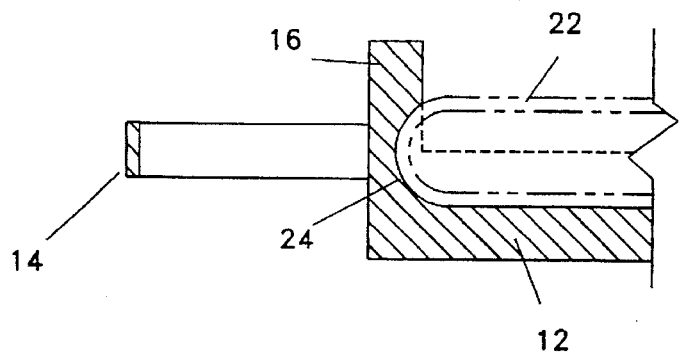
FIG. 4 is a sectional view of the multiple draw syringe taken along line 4—4 of FIG. 1.
Figure 5:
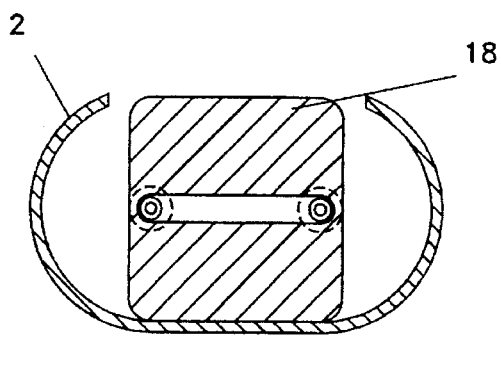
FIG. 5 is a sectional view of the multiple draw syringe taken along line 5—5 of FIG. 2.

Referring now to FIG. 4, the forward face of the rearward wall 16 of said plunger tray 12 includes a plurality of rear tube depressions 24 equal in number to and connected with and aligned with said tube depressions 20. The rear tube depressions 24 have a generally hemispherical shape and when evacuated tubes 22 are placed in said tube depressions 20, the rearward ends of said evacuated tubes 22 fit into said rear tube depressions 24.

Figure 2:
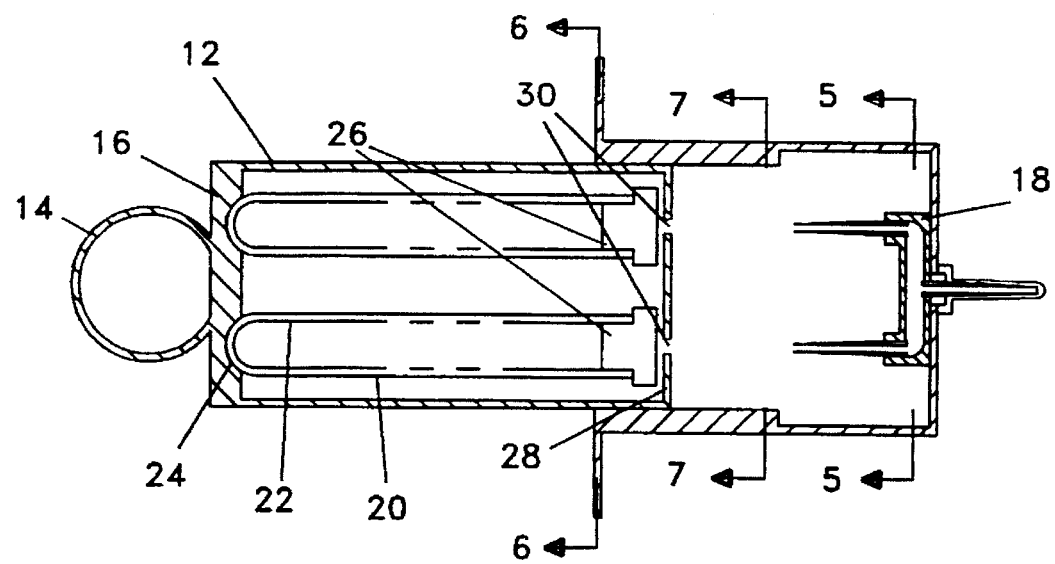
FIG. 2 is a sectional view of the multiple draw syringe taken along line 2—2 of FIG. 1.

Referring now to FIG. 2, said evacuated tubes 22 have stoppers 26 inserted into their tops. Said tube depressions 20 are configured to accept the stoppers 26 as well as said evacuated tubes 22. The forward wall 28 of said plunger tray 12 is approximately the same height as said rearward wall 16. There is a plurality of holes 30 in the forward wall 28 equal in number to the number of said specimen needle slots 10. The holes 30 are aligned with the centers of the forward faces of said stoppers 26.

Figure 9:
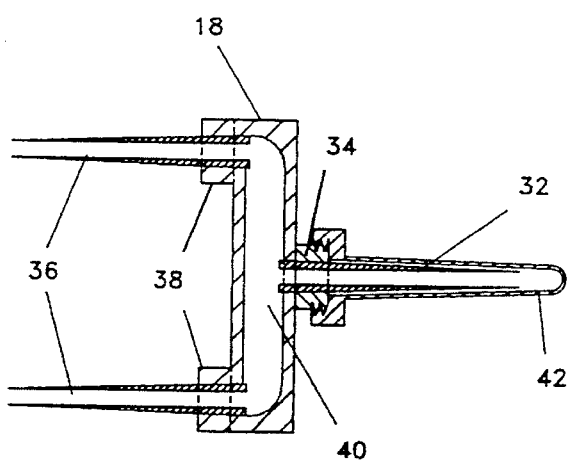
FIG. 9 is a sectional view of the multiple draw syringe taken along line 9—9 of FIG. 8.

Referring now to FIG. 9, the needle manifold 18 has the general shape of a flat box with a width slightly less than the length of said manifold slot 8, a thickness slightly less than the width of said manifold slot 8, and a height slightly less than the interior height of said protective barrel 2. Said needle manifold 18 includes a hollow drawing needle 32 which protrudes forward from the forward face of said needle manifold 18. A drawing needle collar 34 having a generally cylindrical shape and attached to the forward face of said needle manifold 18 helps to hold the drawing needle 32 in place. The forward end of the drawing needle collar 34 is exteriorly screw threaded. A plurality of hollow specimen needles 36, equal in number to the number of said specimen needle slots 10, protrude rearward from the rearward face of said needle manifold 18. Specimen needle collars 38 having a generally cylindrical shape and attached to the rearward face of said needle manifold 18 help to hold the specimen needles 36 in place. The interior of said needle manifold 18 includes a connecting tube 40 which places the hollow interior of said drawing needle 32 in operational contact with hollow interiors of said specimen needles 36. There is a hollow protective cover 42 slightly larger than said drawing needle 32 which fits over said drawing needle 32.

Figure 10:
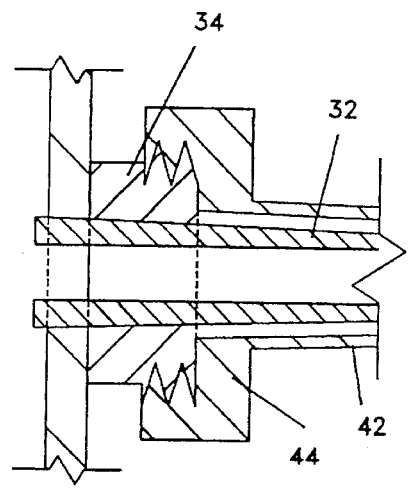
FIG. 10 is an enlarged view of a portion of FIG. 9.
Figures 11, 12:
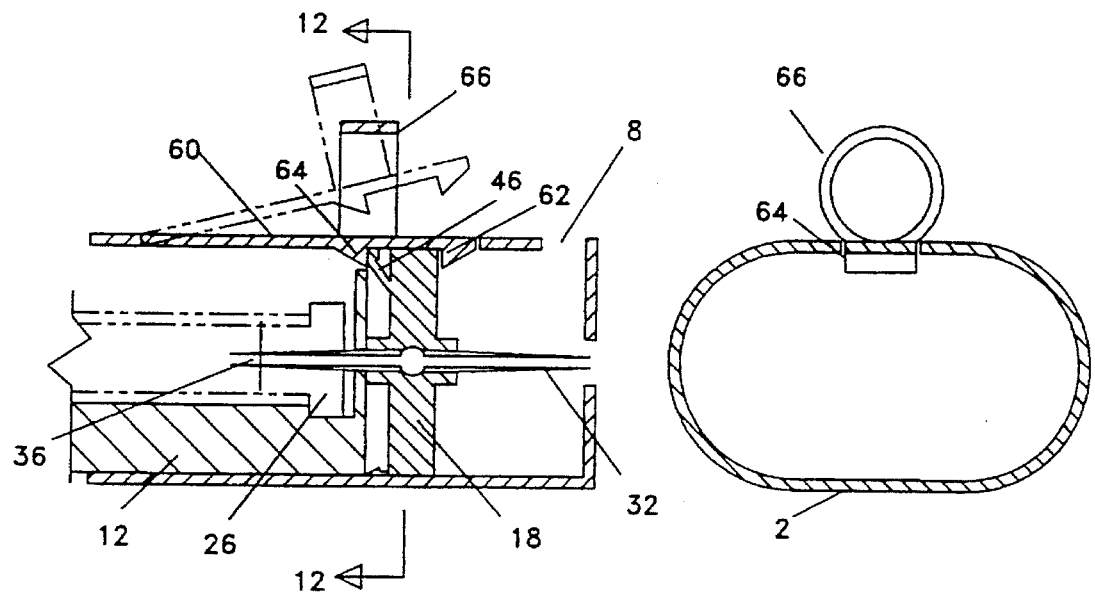
FIG. 11 is a sectional view similar to FIG. 3D, but showing a second embodiment of the present invention.
FIG. 12 is a sectional view of the multiple draw syringe taken along line 12—12 of FIG. 11.

Referring now to FIG. 10, the rearward end of the protective cover 42 includes a cylindrical flange 44. The flange 44 is interiorly screw threaded and said protective cover 42 may be screwed onto the threads on said drawing needle collar 34. The diameter of said drawing needle collar 34 is slightly less than the width of said drawing needle slot 6 and the diameter of said flange 44 is slightly greater than the width of said drawing needle slot 6. The threads in said flange 44 and in said drawing needle collar 34 are configured such that, when said protective cover 42 is screwed onto said drawing needle collar 34, the distance between the rearward end of said protective cover 42 and the forward face of said needle manifold 18 is slightly greater than the thickness of the forward wall of said protective barrel 2.

Figure 8:
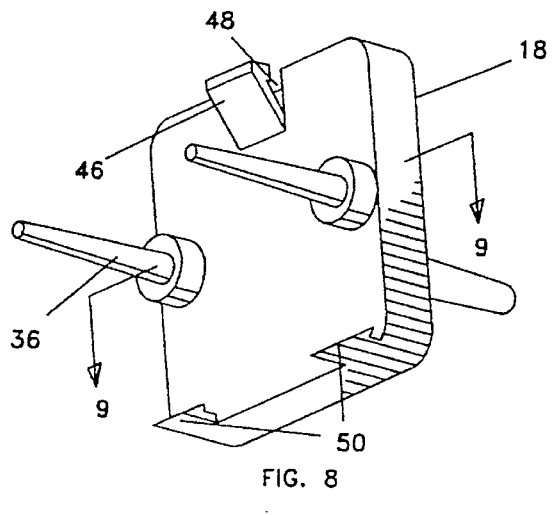
FIG. 8 is a perspective view of a particular element of a of a multiple draw syringe of the present invention.

Referring now to FIG. 8, there is a retaining clip 46 on the rearward face of said needle manifold 18 near the top of said needle manifold 18 and centered on the rearward face of said needle manifold 18. There is a clip hollow 48 in the rearward portion of the top of said needle manifold 18. The clip hollow 48 is an opening aligned with and slightly larger than the retaining clip 46. Two manifold hooks 50 protrude from the bottom of the rearward face of said needle manifold 18. The manifold hooks 50 are the same distance apart as the two outermost of said specimen needle slots 10 and slightly smaller than the width of said specimen needle slots 10.

Referring again to FIG. 1, said needle manifold 18 may be inserted through said manifold slot 8. Said specimen needles 36 pass through said specimen needle slots 10. Said drawing needle collar 34 slides downward within said drawing needle slot 6.

Figure 3A:
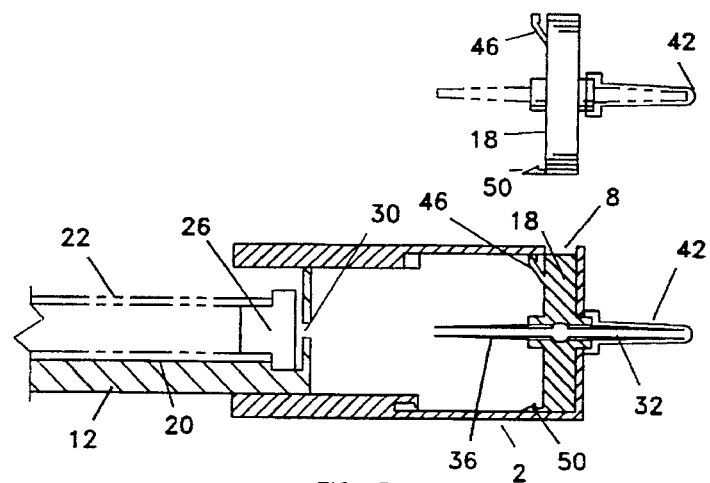
FIGS. 3A, 3B, 3C, and 3D are sectional views of the multiple draw syringe taken along line 3—3 of FIG. 1. These four figures depict the same elements in alternate positions.

Referring now to FIG. 3A, as said needle manifold 18 is pressed into said protective barrel 2, said retaining clip 46 is sufficiently flexible to be forced forward into said clip hollow 48 as said retaining clip 46 passes the rearward edge of said manifold slot 8. After said retaining clip 46 passes the rearward edge of said manifold slot 8, said retaining clip 46 springs back rearward and the top of said retaining clip 46 contacts the underside of the top of said protective barrel 2, holding said needle manifold 18 in place. The rearward face of said flange 44 contacts the forward face of said protective barrel 2, further holding said needle manifold 18 in place within said protective barrel 2. Said evacuated tubes 22 may be placed into said tube depressions 20 and the forward end of said plunger tray 12 inserted into the rearward end of said protective barrel 2.

Referring again to FIG. 1, after said plunger tray 12 is inserted into the rearward end of said protective barrel 2, as described in the preceding paragraph, the multiple draw syringe is held in one hand with the thumb in said plunger control ring 14 and the fingers around said finger control wings 4.

Figure 3B:
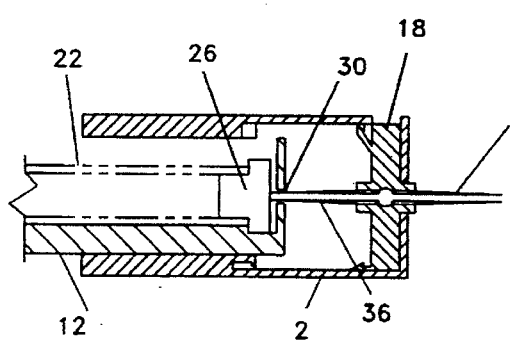

Referring now to FIG. 3B, said plunger tray 12 is pressed forward into said protective barrel 2 until the rearward ends of said specimen needles 36 pass through said holes 30 and contact the forward faces of said stoppers 26. Sufficient pressure is exerted to hold the ends of said specimen needles 36 against said stoppers 26 and to hold said needle manifold 18 against the inside of the forward wall of said protective barrel 2 without puncturing said stoppers 26. Said protective cover 42 is unscrewed and removed. The forward end of said drawing needle 32 is inserted into the vessel or other fluid carrier from which the fluid sample is to be withdrawn.

Figure 3C:
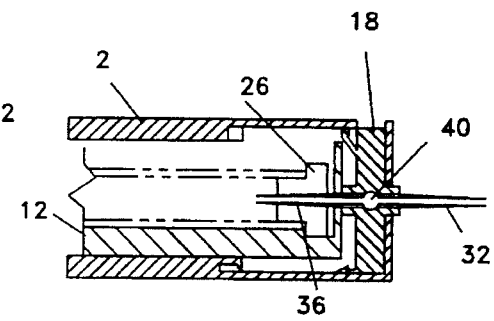

Referring now to FIG. 3C, after said drawing needle 32 is inserted, said plunger tray 12 is pressed all the way forward within said protective barrel 2. Said specimen needles 36 puncture said stoppers 26 and extend into the interior of said evacuated tubes 22. The vacuum in said evacuated tubes 22 and any pressure in the sampled vessel causes the sample fluid to flow through said drawing needle 32, into said connecting tube 40, through said specimen needles 36, and into said evacuated tubes 22.

Figure 3D:
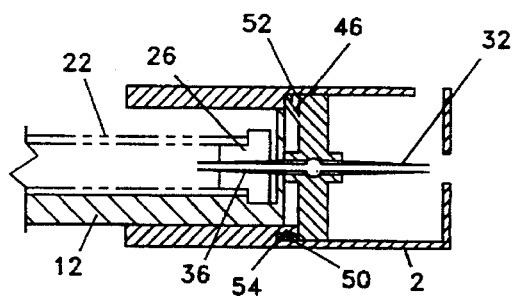

Referring now to FIG. 3D, after said evacuated tubes are filled with the required sample, said drawing needle 32 is withdrawn and said plunger tray 12 is pulled rearward until said retaining clip 46 hits a retaining clip acceptor 52 in said protective barrel 2 and said manifold hooks 50 engage manifold latches 54. At this point needle manifold 18 including said drawing needle 32 and said specimen needles 36 are completely enclosed by and secured within said protective barrel 2. Said plunger tray may be withdrawn from said protective barrel 2 and said evacuated tubes 22 taken from said plunger tray 12. Said protective barrel 2 and said needle manifold 18 may be safely discarded.

Figure 3E:
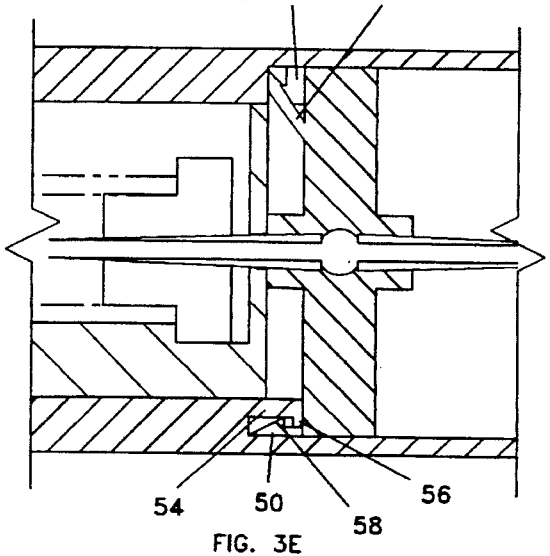
FIG. 3E is an enlarged view of a portion of FIG. 3D.
Figure 7:
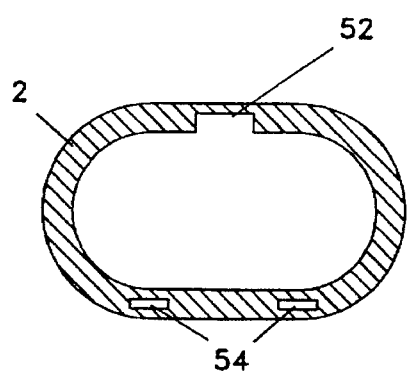
FIG. 7 is a sectional view of the multiple draw syringe taken along line 7—7 of FIG. 2.

Referring now to FIG. 3E which shows an enlarged view of a portion of FIG. 3D, the latch mechanism is shown in greater detail. The rearward portion of the walls of said protective barrel 2 is thicker than the forward portion. The manifold latches 54 are essentially hollows within the thicker wall of said protective barrel 2 aligned with said manifold hooks 50. Latch lips 56 protrude downward from the top of the forward edges of the manifold latches 54. The rearward edge of said manifold hooks 50 form wedge shaped hook stops 58. When said needle manifold 18 is pulled rearward as indicated above, the thin, rearward edge of the hook stops 58 slide into said manifold latches 54. The wider, forward portions of said hook stops 58 engage the rearward faces of the latch lips 56 and, thus, secure said needle manifold 18 within said protective barrel 2. FIG. 7 shows said manifold latches 54 and the retaining clip acceptor 52 in cross section.

FIGS. 11, 12, and 13 depict a second embodiment of the multiple draw syringe. FIG. 11 is similar to FIG. 3D. The process of collecting the fluid sample is the same as previously described. Said needle manifold 18 is the same as previously described. Said protective barrel 2 is also the same as previously described with a few exceptions. The walls of the rearward portion of said protective barrel 2 are not thicker than the wall of the forward portion in the second embodiment and there is neither a retaining clip acceptor 52 nor manifold latches 54. Referring now to FIG. 11, there is a manifold retainer 60 in the center of the rearward portion of said protective barrel 2. The manifold retainer 60 is made by making three cuts in the top of said protective barrel 2: one at the front of said manifold retainer 60, one at the back of said manifold retainer 60, and one at the forward end of said manifold retainer 60. A forward stop 62 at the forward end of said manifold retainer 60 protrudes downward into said protective barrel 2. The forward stop 62 has the general shape of a wedge with the narrow portion of the wedge facing forward. There is a rearward stop 64 also attached to said manifold retainer 60 and aligned with said forward stop 62. The rearward stop 64 has the general shape of a wedge with the narrow portion of the wedge facing rearward. The distance between the rearward face of said forward stop 62 and the forward face of said rearward stop 64 is slightly greater than the distance between the rearward face of said retaining clip 46 and the forward face of said needle manifold 18. A retainer ring 66 is attached to the top of the forward end of said manifold retainer 60. The retainer ring 66 has the general shape of a short cylinder with the ends of the cylinder parallel to said manifold slot 8. The rearward end of said manifold retainer 60 affixed to the top of said protective barrel 2 tends to hold said manifold retainer 60 aligned with the top of said protective barrel 2; however, the forward end of said manifold retainer 60 may be forced temporarily upward from the top of said protective barrel 2. When said plunger tray 12 is pulled from said protective barrel 2, said retaining clip 46 contacts the forward face of said forward stop 62 and forces said manifold retainer temporarily upward until the forward face of said needle manifold 18 passes the rearward face of said forward stop 62. Said manifold retainer 60 then returns to its position aligned with the top of said protective barrel 2. Said retaining clip 46 hits the forward face of the rearward stop 64 and said specimen needles 36 are pulled from said stoppers 26. Said needle manifold 18 remains inside said protective barrel 2 and is held inside between said forward stop 62 and said rearward stop 64. Said manifold retainer 60 may then be pulled away from said protective barrel 2 using said retainer ring 66 as shown by the phantom line image of said manifold retainer 60. Said protective barrel 2 may then be upended and said needle manifold 18 will fall from said protective barrel 2 and may be safely discarded. Said protective barrel 2 and said plunger tray 12 may then be reused.

Referring now to FIG. 13, a perspective view of the embodiment of the multiple draw syringe depicted in FIGS. 11 and 12 is shown. Only said protective barrel 2 is shown and said manifold retainer 60 is shown pulled upward and away from said protective barrel 2 as described in the previous paragraph.

In the preferred embodiment of the multiple draw syringe all parts unless further specified below are made from a tough, non-toxic, sterilizable plastic sufficiently stiff to provide the necessary rigidity; but sufficiently flexible to allow necessary movement of elements such as said manifold clip 46 and said manifold retainer 60. However, it is possible that other materials such as aluminum or the like could be used. Said drawing needle 32 and said specimen needles 36 are made of stainless steel in the preferred embodiment; however, other materials including plastic could be used. In the preferred embodiment said plunger tray 12, said needle manifold 18, and said protective barrel 2 are injection molded and tooled where necessary, but other methods of manufacture could be used. In the preferred embodiment said protective barrel 2 and said needle manifold 18 are made of two pieces glued or plastic welded together, and said plunger tray 12 is made of single piece; however other methods of manufacture could be used. All necessary joints and connections are glued, but methods of manufacture including welding or methods not requiring joints or connections or other joining or connecting methods could be used. In the preferred embodiment said protective cover 42 is screwed onto said drawing needle collar 34;,however, said protective cover 42 could be pressed onto said drawing needle collar 34 and held in place by friction between the two elements rather than by screw threads.

While preferred embodiments of this invention have been shown and described above, it will be apparent to those skilled in the an that various modifications may be made in these embodiments without departing from the spirit of the present invention. For that reason, the scope of the invention is set forth in the following claims:

I claim:

1. A multiple draw syringe for drawing multiple fluid samples into a plurality of conventional, stoppered, evacuated, sample tubes comprising:

(1) a protective barrel being hollow and having an open rearward face, a forward face, and a top face; the forward face having a slot perpendicular to the top face; said top face having an opening at the end of said top face nearest said forward face such that the opening in said top face is connected with the slot in said forward face;

(2) a plunger tray having a rearward end, a forward end, and a bottom; the forward end of the plunger tray being capable of being inserted into the open rearward face of the protective barrel; said plunger tray being adapted to hold a plurality of stoppered, evacuated, sample tubes such that the stoppered, evacuated, sample tubes are perpendicular to said forward end of said plunger tray and the stoppered ends of said stoppered, evacuated, sample tubes are adjacent to said forward end of said plunger tray; and (3) a needle manifold having a rearward face and a forward face; the needle manifold being capable of being inserted into the interior of said protective barrel through the opening in said top face of said protective barrel; said needle manifold having a hollow drawing needle projecting forward from the forward face of said needle manifold such that the hollow drawing needle protrudes forward through said slot in said forward face of said protective barrel; said needle manifold having a plurality of hollow specimen needles protruding rearward from the rearward face of said needle manifold; the number of the hollow specimen needles being equal to the number of said stoppered, evacuated, sample tubes held by said plunger tray and one of said hollow specimen needles being aligned with each of said stoppered, evacuated, sample tubes; said needle manifold having an interior tube placing the hollow interior of said hollow drawing needle in operational contact with the hollow interiors of said hollow specimen needles; said needle manifold being adapted such that, if said plunger tray is pressed forward inside said protective barrel, one of said hollow specimen needles pierces the stoppered top of each of said stoppered, evacuated, sample tubes and places the interior of said stoppered, evacuated, sample tubes in operational contact with the hollow interiors of said hollow specimen needles;

whereby conventional, stoppered, evacuated, sample tubes may be placed within said plunger tray with the stoppers toward said forward face of said plunger tray; said plunger tray may be inserted into the rearward end of said protective barrel; and said needle manifold may be inserted through said opening in said top of said protective barrel into said protective barrel with said hollow drawing needle protruding forward from the forward end of said protective barrel; said plunger tray may be pushed forward into said protective barrel until the rearward ends of said hollow specimen needles press against the tops of the stoppers; said hollow drawing needle may be inserted into a vessel from which a fluid sample is to be taken; said plunger tray may be pushed further forward causing said hollow specimen needles to puncture the stoppers of said stoppered, evacuated, sample tubes and placing said hollow drawing needle in operational contact with the interiors of said stoppered, evacuated, sample tubes; and the fluid to be sampled flows from the vessel from which a fluid sample is to be taken, through said needle manifold, and into said stoppered, evacuated, sample tubes.

2. A multiple draw syringe of claim 1 in which locking means is included to lock said needle manifold inside said protective barrel after the multiple draw syringe has been used such that said needle manifold, said hollow drawing needle, and said hollow specimen needles are completely enclosed within said protective barrel.

3. A multiple draw syringe of claim 1 in which cover means is included to cover said hollow drawing needle after said hollow drawing needle is in position protruding forward from said forward face of said protective barrel; the cover means adapted to safely cover said hollow drawing needle and to hold said needle manifold in position with said hollow drawing needle protruding forward from said forward face of said protective barrel.

4. A multiple draw syringe of claim 2 in which cover means is included to cover said hollow drawing needle after said hollow drawing needle is in position protruding forward from said forward face of said protective barrel; the cover means adapted to safely cover said hollow drawing needle and to hold said needle manifold in position with said hollow drawing needle protruding forward from said forward face of said protective barrel.

5. A multiple draw syringe for drawing multiple fluid samples into a plurality of conventional, stoppered, evacuated, sample tubes comprising:

(1) a protective barrel being hollow and having an open rearward face, a forward face, and a top face; the forward face having an opening;

(2) a plunger tray having a rearward end, a forward end, and a bottom; the forward end of the plunger tray being capable of being inserted into the open rearward face of the protective barrel; said plunger tray being adapted to hold a plurality of stoppered, evacuated, sample tubes such that the stoppered, evacuated, sample tubes are perpendicular to said forward end of said plunger tray and said stoppered ends of said stoppered, evacuated, sample tubes are adjacent to said forward end of said plunger tray; and (3) a needle manifold having a rearward face and a forward face; the needle manifold being inside said protective barrel; said needle manifold having a hollow drawing needle projecting forward from the forward face of said needle manifold such that the hollow drawing needle protrudes forward through said opening in said forward face of said protective barrel; said needle manifold having a plurality of hollow specimen needles protruding rearward from the rearward face of said needle manifold; the number of the hollow specimen needles being equal to the number of stoppered, evacuated, sample tubes held by said plunger tray and one of said hollow specimen needles being aligned with each of said stoppered, evacuated, sample tubes; said needle manifold having an interior tube placing the hollow interior of said hollow drawing needle in operational contact with the hollow interiors of said hollow specimen needles; said needle manifold being adapted such that, if said plunger tray is pressed forward inside said protective barrel, one of said hollow specimen needles pierces said stoppered top of each of said stoppered, evacuated, sample tubes and places the interior of said stoppered, evacuated, sample tubes in operational contact with the hollow interiors of said hollow specimen needles;

whereby conventional, stoppered, evacuated, sample tubes may be placed within said plunger tray with the stoppers toward said forward face of said plunger tray; said plunger tray may be inserted into the rearward end of said protective barrel; and said needle manifold is inside said protective barrel with said hollow drawing needle protruding forward from the forward end of said protective barrel; said plunger tray may be pushed forward into said protective barrel until the rearward ends of said hollow specimen needles press against the tops of the stoppers; said hollow drawing needle may be inserted into a vessel from which a fluid sample is to be taken; said plunger tray may be pushed further forward causing said hollow specimen needles to puncture the stoppers of said stoppered, evacuated, sample tubes and placing said hollow drawing needle in operational contact with the interiors of said stoppered, evacuated, sample tubes; and the fluid to be sampled flows from the vessel from which a fluid sample is to be taken, through said needle manifold, and into said stoppered, evacuated, sample tubes.

6. A multiple draw syringe of claim 5 in which locking means is included to lock said needle manifold inside said protective barrel after the multiple draw syringe has been used such that said needle manifold, said hollow drawing needle, and said hollow specimen needles are completely enclosed within said protective barrel.

7. A multiple draw syringe of claim 5 in which cover means is included to cover said hollow drawing needle after said hollow drawing needle is in position protruding forward from said forward face of said protective barrel; the cover means adapted to safely cover said hollow drawing needle and to hold said needle manifold in position with said hollow drawing needle protruding forward from said forward face of said protective barrel.

8. A multiple draw syringe of claim 6 in which cover means is included to cover said hollow drawing needle after said hollow drawing needle is in position protruding forward from said forward face of said protective barrel; the cover means adapted to safely cover said hollow drawing needle and to hold said needle manifold in position with said hollow drawing needle protruding forward from said forward face of said protective barrel.

9. A multiple draw syringe for drawing multiple fluid samples into a plurality of conventional, stoppered, evacuated, sample tubes comprising:

(1) a protective barrel being hollow and having an open rearward face, a forward face, the forward face having an opening:

(2) a plunger tray having a rearward end, a forward end, and a bottom; the forward end of the plunger tray being capable of being inserted into the open rearward face of said protective barrel; said plunger tray being adapted to hold a plurality of stoppered, evacuated, sample tubes such that the stoppered, evacuated, sample tubes are perpendicular to said forward end of said plunger tray and said stoppered ends of said stoppered, evacuated, sample tubes are adjacent to said forward end of said plunger tray; and (3) a needle manifold having a rearward face and a forward face; the needle manifold being inside said protective barrel; said needle manifold having a hollow drawing needle projecting forward from the forward face of said needle manifold such that the hollow drawing needle protrudes forward through said opening in said forward face of said protective barrel; said needle manifold having a plurality of hollow specimen needles protruding rearward from the rearward face of said needle manifold; the number of the hollow specimen needles being equal to the number of stoppered, evacuated, sample tubes held by said plunger tray and one of said hollow specimen needles being aligned with each of said stoppered, evacuated, sample tubes; said needle manifold having an interior tube placing the hollow interior of said hollow drawing needle in operational contact with the hollow interiors of said hollow specimen needles; said needle manifold being adapted such that, if said plunger tray is pressed forward inside said protective barrel, one of said hollow specimen needles presses against said stoppered top of each of said stoppered, evacuated, sample tubes, said hollow drawing needle may be inserted into the fluid to be sampled, said plunger tray may be pressed further forward until one of said hollow specimen needles pierces said stoppered top of each of said stoppered, evacuated, sample tubes and places the interior of said stoppered, evacuated, sample tubes in operational contact with the hollow interiors of said hollow specimen needles, the fluid to be sampled flows into said stoppered, evacuated, sample tubes, said plunger tray may be pulled rearward and withdrawn from the rearward end of said protective barrel, said needle manifold is pulled rearward with said plunger tray;

whereby conventional, stoppered, evacuated, sample tubes may be placed within said plunger tray with the stoppers toward said forward face of said plunger tray; said plunger tray may be inserted into the rearward end of said protective barrel; and said needle manifold is inside said protective barrel with said hollow drawing needle protruding forward from the forward end of said protective barrel; said plunger tray may be pushed forward into said protective barrel until the rearward ends of said hollow specimen needles press against the tops of the stoppers; said hollow drawing needle may be inserted into a vessel from which a fluid sample is to be taken; said plunger tray may be pushed further forward causing said hollow specimen needles to puncture the stoppers of said stoppered, evacuated, sample tubes and placing said hollow drawing needle in operational contact with the interiors of said stoppered, evacuated, sample tubes; and the fluid to be sampled flows from the vessel from which a fluid sample is to be taken, through said needle manifold, and into said stoppered, evacuated, sample tubes.

10. A multiple draw syringe of claim 9 in which locking means is included to lock said needle manifold inside said protective barrel after the multiple draw syringe has been used such that said needle manifold, said hollow drawing needle, and said hollow specimen needles are completely enclosed within said protective barrel.

11. A multiple draw syringe of claim 9 in which cover means is included to cover said hollow drawing needle after said hollow drawing needle is in position protruding forward from said forward face of said protective barrel; the cover means adapted to safely cover said hollow drawing needle and to hold said needle manifold in position with said hollow drawing needle protruding forward from said forward face of said protective barrel.

12. A multiple draw syringe of claim 10 in which cover means is included to cover said hollow drawing needle after said hollow drawing needle is in position protruding forward from said forward face of said protective barrel; the cover means adapted to safely cover said hollow drawing needle and to hold said needle manifold in position with said hollow drawing needle protruding forward from said forward face of said protective barrel.

* * * * *